United States Patent [19]

Burney et al.

[11] Patent Number: 6,010,514

[45] Date of Patent: Jan. 4, 2000

[54] SUTURING ASSEMBLY AND METHOD OF USE

[76] Inventors: Bryan T. Burney, 10421 Fall Creek Rd., Fishers, Ind. 46256; Michael E. Miller, 4560 West WoodPecker La., Trafalgar, Ind. 46181

[21] Appl. No.: 09/042,956

[22] Filed: Mar. 17, 1998

[51] Int. Cl.$^7$ .................................................. A61B 17/04
[52] U.S. Cl. ............................................................ 606/144
[58] Field of Search .................................... 606/148, 144, 606/139, 207, 146

[56] References Cited

U.S. PATENT DOCUMENTS

| | | |
|---|---|---|
| 312,408 | 2/1885 | Wackerhagen . |
| 659,422 | 10/1900 | Shidler . |
| 2,646,045 | 7/1953 | Priestley . |
| 2,959,172 | 11/1960 | Held . |
| 3,470,875 | 10/1969 | Johnson . |
| 3,665,926 | 5/1972 | Flores . |
| 4,317,445 | 3/1982 | Robinson . |
| 4,493,323 | 1/1985 | Albright et al. . |
| 4,553,543 | 11/1985 | Amarasinghe . |
| 4,587,969 | 5/1986 | Gillis . |
| 4,629,450 | 12/1986 | Suzuki et al. . |
| 4,744,364 | 5/1988 | Kensey . |
| 4,852,568 | 8/1989 | Kensey . |
| 4,890,612 | 1/1990 | Kensey . |
| 4,929,246 | 5/1990 | Sinofsky . |
| 5,021,059 | 6/1991 | Kensey et al. . |
| 5,059,201 | 10/1991 | Asnis . |
| 5,061,274 | 10/1991 | Kensey . |
| 5,129,912 | 7/1992 | Noda et al. . |
| 5,160,339 | 11/1992 | Chen et al. . |
| 5,171,251 | 12/1992 | Bregen et al. . |
| 5,180,385 | 1/1993 | Sontag . |

(List continued on next page.)

FOREIGN PATENT DOCUMENTS

| | | |
|---|---|---|
| 0140557 | 8/1985 | European Pat. Off. . |
| 1093329 | 5/1984 | U.S.S.R. . |
| 1174036 | 8/1985 | U.S.S.R. . |
| WO94/05213 | 3/1994 | WIPO . |
| WO97/00046 | 1/1997 | WIPO . |

OTHER PUBLICATIONS

Gianturco, Michael, "A Play on Catheterization," Forbes, p. 146, (Dec. 30, 1996).

Alexander, Walter, "Advances in Interventional Cardiology HIgher Risk Patients Demand Greater Vigilance, " Today's Surgical Nurse, p. 11–15, (Jun. 23, 1996).

"Kensey Nash Angio–Seal to be Available Oct. 21," M–D–D–I Reports —"The Gray Sheet, " p. I&W–2 and I&W–3 (Oct. 7, 1996).

*Primary Examiner*—Michael Buiz
*Assistant Examiner*—(Jackie)Tan-Uyen T Ho
*Attorney, Agent, or Firm*—Baker & Daniels

[57] ABSTRACT

A suturing assembly is provided which includes a cannula with first and second ends. A first portion adjacent the first end defines a proximal lumen for slidably receiving a needle, a first bend and a needle exit aperture at the first bend in communication with the proximal lumen. The first lumen and the needle exit aperture define a needle path. A second portion is adjacent the second end and defines a distal lumen. The cannula defines a second bend between the first bend and the second portion. A needle entrance aperture is defined in the second portion in communication with the distal lumen and in line with the needle path. The cannula defines a first opening in the first end in communication with the proximal lumen. A needle with a piercing end is slidably disposed within the proximal lumen. The needle has a first position within the proximal lumen and a second deployed position with the piercing end in the distal lumen and the opposite end in the proximal lumen. A suture is secured to the needle and extends through the proximal lumen, the exit aperture, the entrance aperture and the second opening. Methods are also provided which include inserting the first end of the cannula into a wound so that the exit aperture contacts an inner surface of tissue surrounding the wound and deploying the piercing end of the needle through the needle exit aperture, the tissue and into the entrance aperture by applying a force on the suture extending from the second end.

21 Claims, 7 Drawing Sheets

U.S. PATENT DOCUMENTS

| | | | |
|---|---|---|---|
| 5,192,302 | 3/1993 | Kensey et al. | |
| 5,211,650 | 5/1993 | Noda. | |
| 5,222,974 | 6/1993 | Kensey et al. | |
| 5,230,424 | 7/1993 | Alpern et al. | |
| 5,236,083 | 8/1993 | Sobel et al. | |
| 5,282,809 | 2/1994 | Kammerer et al. | |
| 5,282,827 | 2/1994 | Kensey et al. | |
| 5,304,184 | 4/1994 | Hathaway et al. | |
| 5,306,254 | 4/1994 | Nash et al. | |
| 5,320,629 | 6/1994 | Noda et al. | |
| 5,320,632 | 6/1994 | Heidmueller. | |
| 5,350,385 | 9/1994 | Christy. | |
| 5,364,408 | 11/1994 | Gordon. | |
| 5,368,601 | 11/1994 | Sauer et al. | |
| 5,374,275 | 12/1994 | Bradley et al. | |
| 5,387,221 | 2/1995 | Bisgaard. | |
| 5,391,182 | 2/1995 | Chin. | |
| 5,411,481 | 5/1995 | Allen et al. | |
| 5,417,699 | 5/1995 | Klein et al. | |
| 5,613,974 | 3/1997 | Andreas et al. | |
| 5,618,290 | 4/1997 | Toy et al. | |
| 5,800,389 | 9/1998 | Burney et al. | |
| 5,810,849 | 9/1998 | Kontos | 606/144 |
| 5,855,585 | 1/1999 | Kontos | 606/144 |
| 5,876,411 | 3/1999 | Kontos | 606/144 |

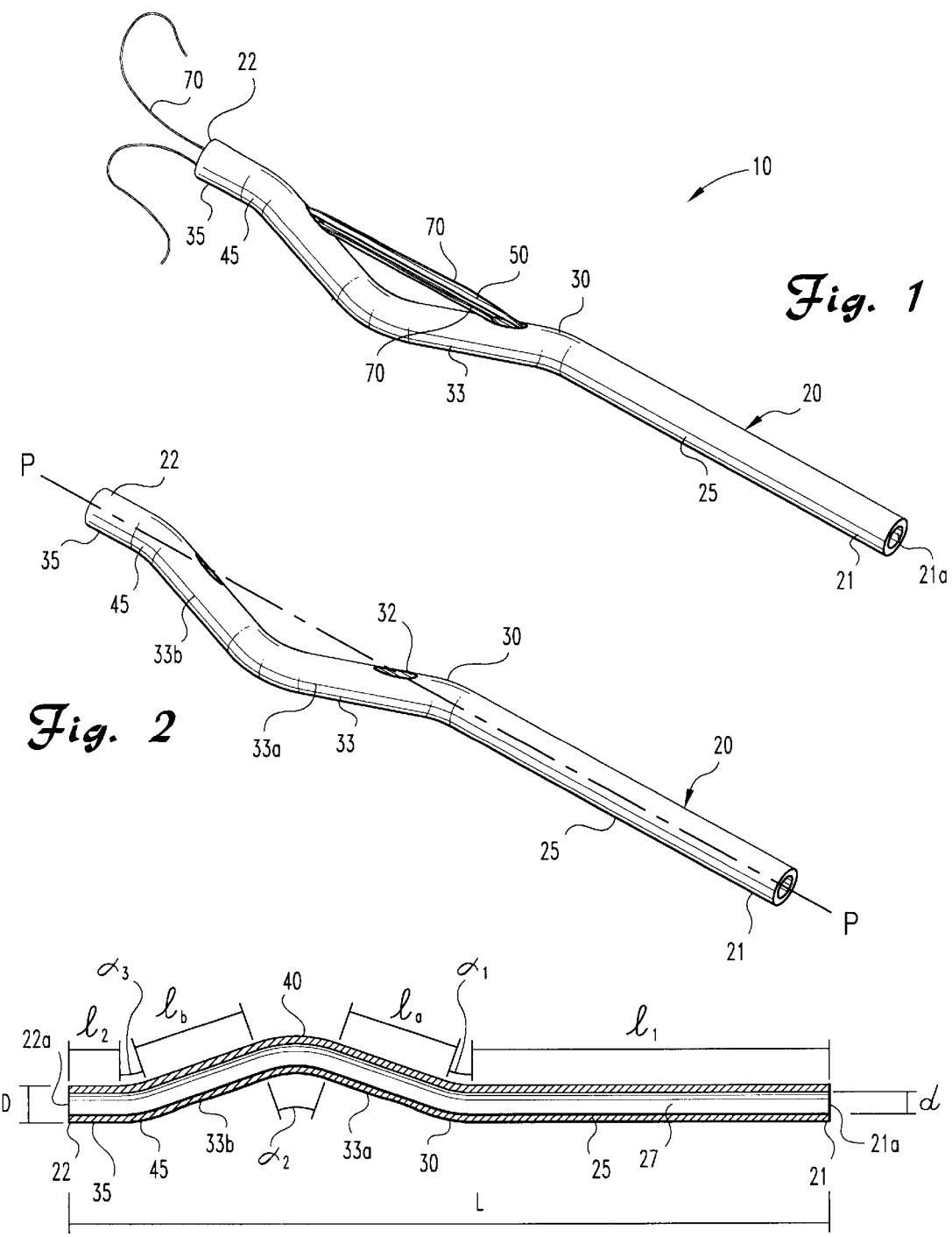
Fig. 1
Fig. 2
Fig. 3
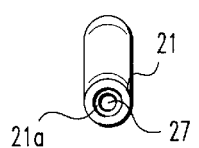
Fig. 4

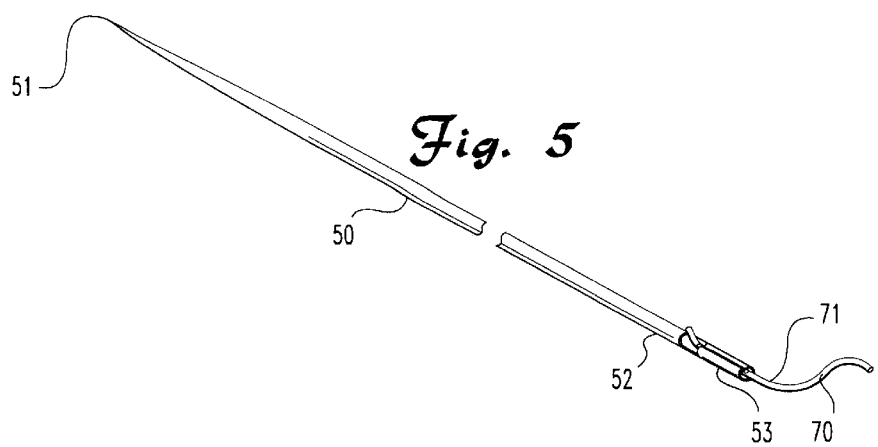
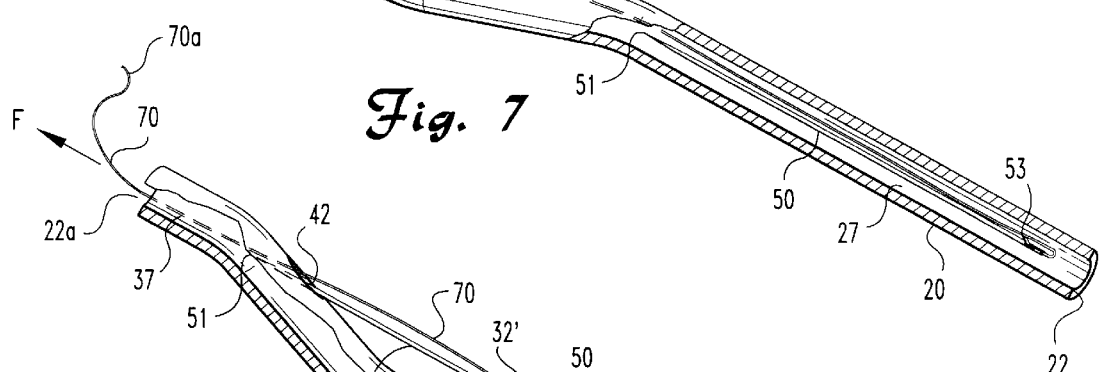
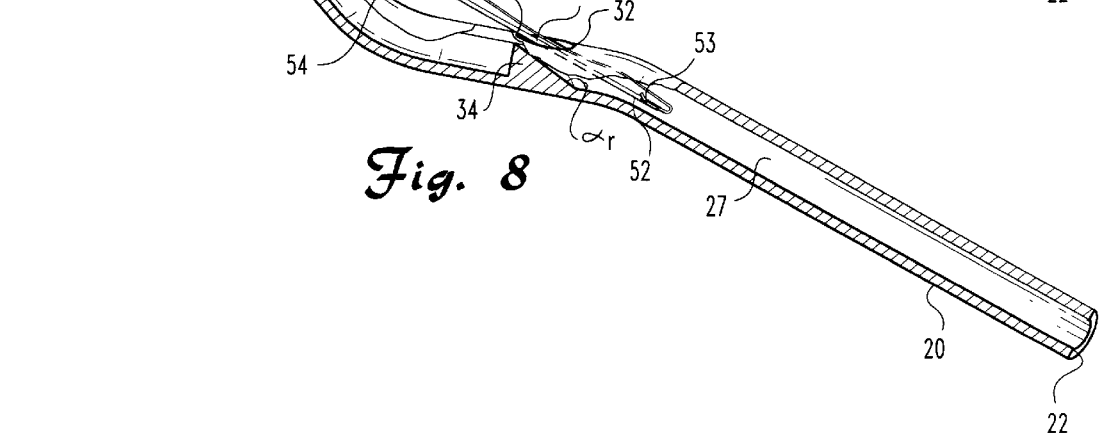

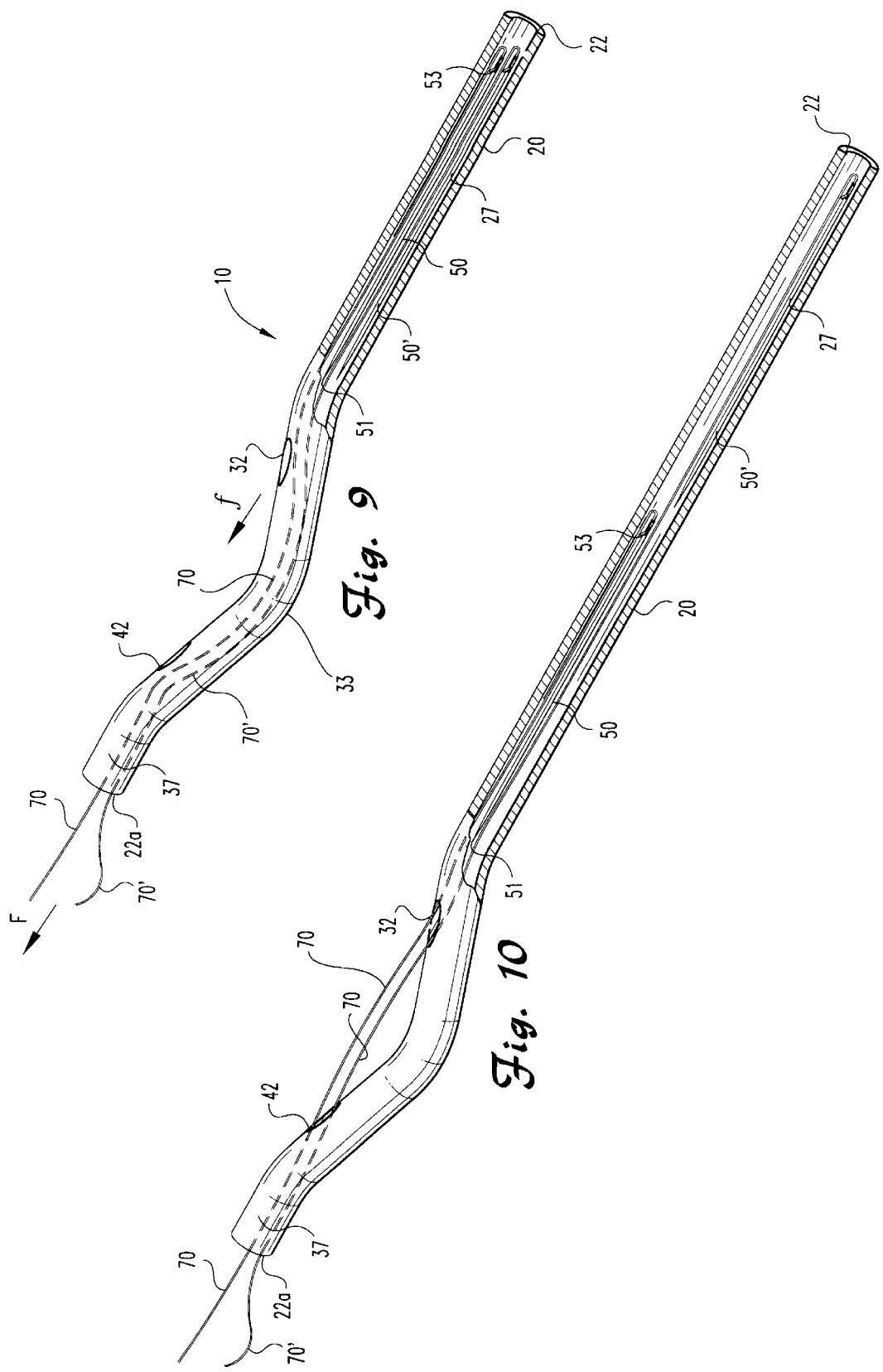

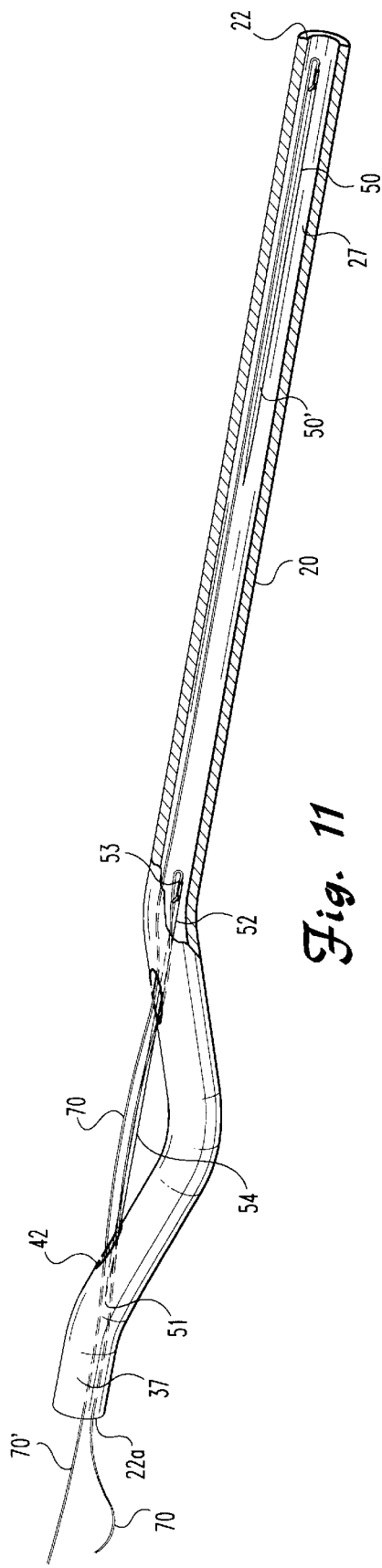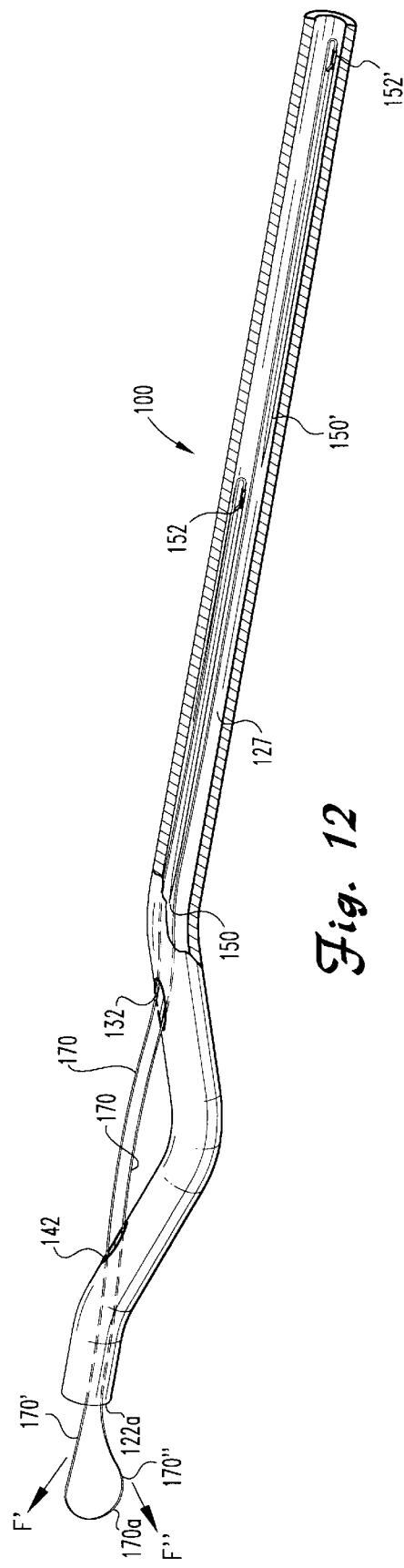

SUTURING ASSEMBLY AND METHOD OF USE

FIELD OF THE INVENTION

The present invention relates generally to medical devices and methods of use. More specifically, the present invention relates to devices and methods for the percutaneous closure of arterial, venous and other puncture sites.

BACKGROUND OF THE INVENTION

A number of diagnostic and therapeutic vascular procedures are now performed transluminally, where a catheter is introduced through an introducer sheath to the vascular system at a convenient access site and guided through the vascular system to a target location. Such intravascular procedures, include angiographic dye injection, cardiac catheterizations, balloon angioplasty, stent therapy and other types of recanalizing of atherosclerotic arteries and veins.

In these intravascular procedures, an instrument, such as an angiographic needle, is inserted percutaneously through the skin into an artery, such as the femoral artery. A guide wire is then passed through the cannula of the instrument into the artery to the desired depth. Once the guide wire is inserted, the needle cannula is removed, leaving the guidewire in place. An introducer sheath and an arterial dilator or catheter are then passed over the guidewire, through the puncture or incision and into the artery. The guidewire and then the dilator are each removed leaving the introducer sheath or catheter in place. A catheter, or other intravascular instrument, is then inserted through the introducer sheath and threaded down the artery to the desired intravascular location. Because such catheter-based medical procedures require direct vascular access with a vascular puncture, the vascular access site must be closed when the procedure is completed.

When vascular access is no longer required, the introducer sheath is removed and hemostasis is attempted. One common approach is to apply an external force at the puncture site, typically by manual or digital compression. This approach suffers from a number of disadvantages. It is time-consuming, frequently requiring up to one-half hour or more of compression before hemostasis is assured. This procedure is uncomfortable for the patient and frequently requires administering analgesics to be tolerable. Moreover, the application of excessive pressure can at times totally occlude the underlying blood vessel, resulting in ischemia and/or thrombosis.

Following manual compression, the patient is required to remain recumbent for at least four, and at times as long as eighteen, hours under close observation to assure continued hemostasis. During this time, renewed bleeding may occur resulting in bleeding through the tract, hematoma and/or pseudoaneurysm formation as well as arteriovenous fistula formation. These complications may require blood transfusion and/or surgical intervention. The incidence of these complications increases when the sheath size is increased.

The post-procedure hemostasis problem is further aggravated by the use of anticoagulant drug therapy. Such drug therapy is almost always indicated for patients requiring catheter laboratory procedures. Anticoagulants help prevent complications such as coronary artery clots which could cause a heart attack but at the same time, make achieving hemostasis very difficult using conventional methods. Typically, although it is undesirable, anticoagulants are discontinued for several hours so that hemostasis can be achieved. It would be particularly beneficial to achieve hemostasis without the risks associated with discontinuing anticoagulant therapy.

It is clear that the standard technique for arterial closure can be risky, uncomfortable to the patient and expensive due to the need for post procedure observation costs. While the risk of such conditions can be reduced by using highly trained individuals, such use is both expensive and inefficient. If the closure fails and bleeding occurs, the site must be compressed again or vascular surgery is required.

To overcome the problems associated with manual compression, several groups have proposed the use of bioabsorbable fasteners to stop bleeding. A thrombogenic and bioabsorbable material, such as collagen, is placed at the superficial arterial wall over the puncture site. While potentially effective, this approach suffers from a number of problems. It can be difficult to properly locate the interface of the overlying tissue and the adventitial surface of the blood vessel. Furthermore, locating the fastener in the incorrect location can result in failure to provide hemostasis and subsequent hematoma and/or pseudoaneurysm formation. Conversely, if the fastener intrudes into the arterial lumen, intravascular clots and/or collagen pieces with thrombus attached can form and embolize downstream causing vascular occlusion. Also thrombus formation on the surface of a fastener protruding into the lumen can cause a stenosis which can obstruct normal blood flow. Other possible complications include infection as well as adverse reactions to the implant.

One alternative to manual compression and bioabsorbable fasteners is suturing the access site. However, vascular structures are logistically difficult to suture because of their structure and location deep within the body. One device, described in U.S. Pat. No. 5,417,699, includes a shaft for introducing a pair of needles inwardly through the puncture site and then drawing the needles outwardly back through the tissue on either side of the puncture site. The needles are bent so that the pointed ends of the needles can be captured by the device after they have passed through the tissue. The shaft can then be withdrawn to carry the needles and attached suture outwardly back through the tract.

Although this device provides means for immediate closure of a vascular wound, it can damage the vascular structure by increasing the size of the wound to accommodate the device or by tearing the surrounding tissue. Also, because the device delivers each suture simultaneously, the device must be perfectly aligned within the wound. Furthermore, it is not possible to selectively deliver a stitch or to vary the suture pattern. Moreover, the device requires special bendable needles so that the needles can be captured after delivering a suture. The complicated design of the device is fragile and cumbersome and increases the risk of operator failure and device malfunction.

A need has remained for devices and methods which safely and efficiently effect homeostasis after vascular procedures. In particular, a need exists for suturing assemblies which provide means for convenient and efficient suturing of vascular wounds. A need also exists for suturing guides which utilize conventional needles and suture material. A further need has remained for suturing guides which provide flexible suturing patterns.

SUMMARY OF THE INVENTION

The present invention provides suturing assemblies and methods of suturing a vascular system puncture wound. The suturing assembly includes a cannula which defines a first end and a first portion adjacent the first end sized and configured for insertion into a wound. The first portion defines a proximal lumen for slidably receiving a needle, a first bend and a needle exit aperture at the first bend in communication with the proximal lumen. The first lumen and the needle exit aperture define a needle path. The cannula also includes a second end opposite the first end and a second portion which is adjacent the second end and defines a distal lumen. The cannula defines a second bend between the first bend and the second portion. A needle entrance aperture is defined in the second portion in communication with the distal lumen and in line with the needle path. In some embodiments, the cannula defines a first opening in the first end in communication with the proximal lumen and a second opening in the second end in communication with the distal lumen.

A needle is slidably disposed within the proximal lumen. The needle has a piercing end extendable through the needle exit aperture and the needle entrance aperture, and an opposite end slidable within the proximal lumen. The needle has a first position within the proximal lumen and a second deployed position with the piercing end in the distal lumen and the opposite end in the proximal lumen. In some embodiments, a second needle is provided. A suture is secured to the needle and extends through the proximal lumen, the exit aperture, the entrance aperture and the second opening.

Methods are also provided which include inserting the first end of the cannula into a wound so that the exit aperture contacts an inner surface of tissue surrounding the wound and deploying the piercing end of the needle through the needle exit aperture, the tissue and into the entrance aperture to deliver a suture to the tissue. Some methods of the present invention include applying a force on the suture extending from the second end.

One object of the present invention is to provide suturing assemblies and methods for closure of a vascular wound which reduce postoperative care and expense. One advantage of the present invention is that it provides a suturing guide which utilizes standard suturing needles and suturing material.

BRIEF DESCRIPTION OF THE DRAWINGS

FIG. 1 is a side perspective view of a suturing assembly according to one embodiment of this invention.

FIG. 2 is a side perspective view of the suturing guide of the assembly depicted in FIG. 1.

FIG. 3 is a side sectional view of the suturing guide of FIG. 2.

FIG. 4 is an end perspective view of the guide of FIG. 2.

FIG. 5 is a side perspective view of a suture needle.

FIG. 6 is a side perspective view of another suture needle.

FIG. 7 is a partial side sectional view of a suturing assembly of this invention with the needle in the initial position.

FIG. 8 is a side sectional view of a suturing assembly of this invention with the needle in the deployed position.

FIG. 9 is a side partial sectional view of an assembly with the suture threaded through the entire length of the cannula.

FIG. 10 is a side partial view of an assembly having a pair of needle in the initial position.

FIG. 11 is a side partial sectional view of an assembly having one needle in the initial position and one needle in the deployed position.

FIG. 12 is a side partial sectional view of an assembly having a pair of needles in an alternate initial position and employing a single length of suture.

DESCRIPTION OF THE PREFERRED EMBODIMENT

Figure 13:
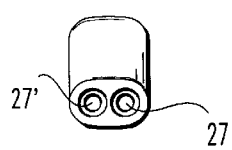
FIG. 13 is an end perspective view of a guide having a pair of lumens.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides suturing assemblies, guides and methods for suturing which provide immediate hemostasis. The wounds can be sutured from the inside out according to this invention. The suturing assemblies of this invention include a curved guide cannula which houses one or more needles in a lumen. The cannula defines a needle exit aperture at one of the curves. The cannula may be placed within a wound with the exit aperture near an edge of the wound. The bend accommodates the edge of the wound so that the needle can be directly aligned underneath the tissue while the practitioner can operate the device from outside the wound. A needle is deployed by a force from outside the wound through the aperture to apply a suture from inside the wound to the outside of the tissue. In preferred embodiments, the suture is threaded backwards from the needle through the lumen. Applying a force to the suture deploys the needle. In most preferred embodiments, the cannula has a second bend which curves it into the needle path. A needle capture aperture defined in the cannula at the intersection of the cannula and the needle path captures the needle. Once the needle is captured by the cannula, the assembly can be removed from the wound pulling the suture through the tissue. This capture feature prevents unnecessary trauma to the patient and needle sticks to the practitioner. The inside out stitch can then be knotted as known in the art. This invention provides a suture guide device of elegant construction which is simple to use but yet provides efficient, reliable suturing in any desired pattern.

The suturing assemblies, devices and methods of this invention have particular utility when used in connection with intravascular procedures, such as angiographic dye injection, cardiac catheterizations, balloon angioplasty and other types of recanalization of atherosclerotic arteries, etc. since they provide immediate hemostasis of the blood vessel, e.g., arterial, puncture. However, it is to be understood that while the description of the preferred embodiments contained herein are directed to the closing off of percutaneous incisions or punctures in arteries, they have much more wide-spread applications, such as closing punctures in other organs generated by diagnostic and therapeutic procedures. For, example, larger diameter punctures, such as those generated by aortic balloon pumps and temporary dialysis procedures, may also be closed according to this invention. Thus, the sealing of a percutaneous opening in an artery shown herein is merely exemplary.

A suturing assembly 10 in accordance with one preferred embodiment of the present invention is depicted in FIGS. 1–12. The assembly 10 includes a cannula 20, a needle 50 and suture material 70. The cannula 20 includes a first end 21 having a first opening 21a and an opposite second end 22 having a second opening 22a. A first portion 25 of the cannula 20 is adjacent the first end 21 and is configured for insertion into a wound. A second portion 35 is adjacent the second end 22 and is configured to be held and manipulated by a human hand. The first and second portions 25, 35 can be of any suitable length $l_1$, $l_2$ and diameter D for the intended application. Lengths $l_1$ and $l_2$ are preferably about 4–5 inches (100–125 mm) and 1.0–2.0 inches (25–50 mm), respectively. In one specific embodiment, the length $l_1$, is about 4.72 inches (120 mm), $l_2$ is about 1.5 inches (37.5 mm) and the diameters D are 0.24 inches (6 mm).

The first portion 25 defines a first or proximal lumen 27 configured for slidably receiving a needle 50. For most procedures the lumen 27 has a diameter d which will accommodate one or more suture needles, generally in the range of 0.08–0.16 inches (2–4 mm). For vascular procedures, d is preferably no larger than about 0.08–0.12 inches (2–3 mm). The first lumen 27 is in communication with the first opening 21a of the cannula 20. The cannula 20 also includes a first bend 30 and a needle exit aperture 32 at or adjacent the first bend 30. Preferably, the bend 30 defines an angle $\alpha_1$, in the range of 150°. The first bend 30 accommodates an edge of wound so the needle can be pulled directly up through the tissue cannula 20 for access by the surgeon to deploy the needle 50. The exit aperture 32 is in communication with the first lumen 27 so that the needle 50 is slidable out of the lumen 27 through the exit aperture 32.

The first lumen 27 and the exit aperture 32 are arranged on an axis to form a needle path P so that the needle 50 can be deployed from the lumen 27 out through the exit aperture 32 to pierce tissue and deliver suture. Because of the location of the bend 30 and the exit aperture 32, a middle portion 33 of the cannula 20 bends away from the needle path P to provide a space for the needle 50 to pierce tissue. In one embodiment, shown in FIG. 8, a ramp 34 is provided in lumen 27 to guide needle 50 to exit aperture 32. Ramp 34 is disposed at one end 32' of exit aperture 32 adjacent the middle portion 33. Ramp 34 is inclined towards exit aperture 32 to guide a needle along needle path P as it advances through the lumen 27. A suture needle 50 will be deflected through the exit aperture 32 and along needle path P as force F is applied to suture 70. Ramp 34 defines an angle $\alpha_r$, which is preferably between about 100° to about 160°. In a most preferred embodiment, angle $\alpha_r$ is about 120°.

The guide or cannula 20 also preferably provides needle capture means which capture the needle after it has delivered a suture to the tissue. This prevents the inclusion of unwanted tissue in the suture and unnecessary trauma to the tissue. The capture means also lowers the risk of needle sticks to the practitioner. In one embodiment, the capture means is provided by a second portion 35 of the cannula 20. As depicted in FIGS. 1–4, the second portion 35 is adjacent the second end 22 and defines a second distal lumen 37. The second lumen 37 is in communication with the second opening 22a at the second end 22 of the cannula 20. In some embodiments, the first and second lumens are portions of a single, continuous lumen defined within the cannula. The cannula preferably includes a second bend 40 between the first bend 30 and the second portion 35. The second bend 40 preferably forms an angle $\alpha_2$ of between about 120° and 150° and divides the middle portion 33 into first 33a and second 33b mid-sections. Most preferably, $\alpha_2$ is about 150°.

The second portion also preferably includes a needle entrance or capture aperture 42. The second bend 40 preferably angles the second portion 35 so that the capture aperture 42 and the second lumen 37 are aligned with the needle path P for receiving a needle. In some embodiments, the cannula 20 also includes a third bend 45 which slightly curves the cannula 20 to better align the capture aperture 42 and distal lumen 37 with the needle path P. The angle $\alpha_3$ of the third bend is preferably in the range of 120° to 170° and most preferably about 150°.

In preferred embodiments, the curved middle portion 33 of the guide 20 is relatively more rigid than the first 25 and second 35 portions so as to displace the surrounding tissue in position near the needle exit aperture 32 when the guide is placed within a wound. On the other hand, the first portion 25 of the guide 20 is preferably composed of a relatively more flexible material so that it will follow the vessel lumen without trauma upon insertion. The portions 25 and 33 can be formed of different materials to achieve this purpose. For example, the cannula 20 can be molded of plastic with an insert in the curved portion 33 to increase stiffness. Other molding techniques which are known in the art, can be used to mold two or more materials with the same mold to form a cannula with desirable stiffness and flexibility characteristics.

The suturing guides of this invention conveniently accept standard suturing needles. One such needle 50 is depicted in FIG. 5 and includes a piercing end 51 and an opposite second end 52. Suture 70 is inserted through an aperture 53 and secured, preferably swedged, to the opposite end 52 of the needle 50. In another embodiment shown in FIG. 6, the opposite end 52' of the needle 50' includes a threading eye 53'.

The needle 50 is slidable within the first 27 and second 37 lumens. As shown in FIG. 7, the needle 50 has an initial ready position within the first lumen 27 with the piercing end 51 adjacent the exit aperture 32 and the opposite end 52 adjacent the second end 22 of the cannula 20. After the needle is deployed through the exit aperture 32 along the needle path P, it is captured by the second lumen 37 through the capture aperture 42. The deployed position of the needle 50 is shown in FIG. 8. In the deployed position the piercing end 51 is inserted into the second lumen 37 with the second end 52 in the first lumen 27. The shaft 54 of the needle 50 rests outside the guide 20 in the needle path P.

The suturing assembly of the present invention conveniently delivers suture of any type to tissue to close wounds or openings in the tissue. One advantage of this invention is that it employs conventional suture material, preferably resorbable suture material. The suture is secured to the needle in any suitable manner. As shown in FIG. 6, the suture material 70 can be threaded through the eye 53' of a needle 50' and tied to a knot 71 or otherwise secured at or near the eye 53'. This provides an anchor in the tissue when the needle 50' is deployed through the tissue. In preferred embodiments, the suture is swedged to the needle 50. The suture 70 is inserted into an aperture 53, such as a trough or hole, which is then crimped around the suture 70. This allows the second end 52 of the needle 50 to have a diameter small enough to accommodate vascular structures.

As shown in FIGS. 7 and 8, the suture material 70 preferably is loaded into the assembly to extend from the opposite end 52 of the needle 50 through the first lumen 27, the exit aperture 32, the entrance aperture 42, the second lumen 37 and out through the second opening 22a. In one embodiment as depicted in FIG. 9, suture material 70 is loaded through the middle portion 33 and does not extend through the exit aperture 32. Applying a pulling force F to the end 70a of the suture extending from the opening 22a applies a force to the opposite end 53 of the needle which deploys the piercing end 51 of the needle 50 through the exit 32. In other words, the suture is threaded backwards so that the suture pulls the needle instead of the needle pulling the suture.

In a most preferred embodiment depicted in FIG. 9, the cannula 20 defines a single continuous lumen which includes the first lumen 27 and the second lumen 37. In this embodiment, the suture can be threaded from the first lumen 27 through the length of the cannula to the second lumen 37 and out through the second opening 22a. Applying a pulling force F to the end 70a of the suture extending from the opening 22a applies a force f to the opposite end 53 of the needle 50 which deploys the piercing end 51 of the needle 50 through the exit 32. One advantage of threading suture this way is that the suture cannot interfere with the needle as it pierces the tissue edge.

In some embodiments, the suturing assembly 10 is provided with more than one needle 50. The needles 50, 50' are disposed along side one another within the first lumen 27 in the initial position as shown in FIG. 9 but they can be deployed independently of one another by pulling the respective suture 70, 70'.

In FIG. 10, the needles 50, 50' are shown sequentially arranged, ie, needle 50 is oriented in a forward initial position in front of needle 50', which is in a second intial position. This embodiment is particularly preferred for percutaneous applications because it allows smaller diameters d and D. The sequential arrangement requires a longer length $l_1$ for the first portion 25. This acceptable because although the diameter D of the cannula may be important in certain applications, the length $l_1$ of the first portion is not critical.

FIG. 11 shows needle 50 in the deployed position and needle 50' in the second initial position within the first lumen 27. Referring again to FIG. 1, both of the needles are in the deployed position. In a most preferred embodiment, a pair of needles 150, 150' share a single suture 170 as shown in FIG. 12. The suture 170 is swedged to the second ends 152, 152' of both of the needles 150, 150'. The suture extends from both of the opposite ends 152, 152' of the needles 150, 150' and extends through the lumen 127, out the exit 132, through the needle entrance 142. The suture 170 exits from the second opening 122a to form a loop 170a.

FIG. 12 depicts the assembly 100 in an initial, ready position according to one preferred embodiment of this invention. In this position, one of the needles 150 is placed in front of the other needle 150'. The first needle 150 is selectively deployed by applying force F' on the first portion 170' of the suture 170. After the first needle 150 has been deployed, the second needle 150' is deployable by applying force F" on the second portion 170" of the suture 170.

Figure 15:
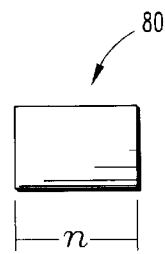
FIG. 15 is a side elevational view of a channel member according to one embodiment of this invention.
Figure 14:
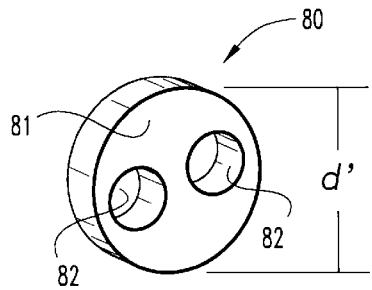
FIG. 14 is an end perspective view of a channel member.
Figure 16:
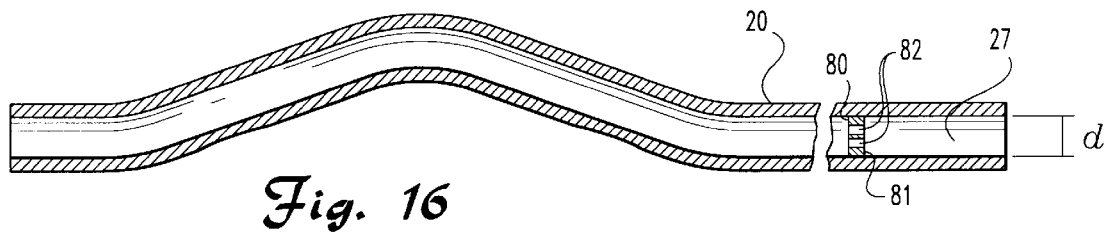
FIG. 16 is a side sectional view of a guide with a channel member for supporting a pair of needles.

In some embodiments intended for multiple needles, channel means is provided for supporting and guiding the needles. In some embodiments the channel means include a second proximal lumen 27' defined in the cannula parallel to the first proximal lumen 27 as depicted in FIG. 13. The second lumen is in communication with the needle deployment aperture and the capture aperture. Any number of lumens may be provided. In preferred embodiments, the channel means includes a channel member 80 as shown in FIGS. 14–16. The channel member 80 includes a support member 81 sized and shaped to be fitted into a lumen of the guide 20, preferably the proximal lumen 27. The support member 81 has a diameter d' which is equal or nearly equal to the diameter d of the lumen. The support is attached or affixed to the guide 20 using any suitable means. For example, the support can be pressfit, molded or glued. The support 81 defines one or more channels 82 which are at least as large as the circumference of a needle. The channels 82 each may receive a needle and where multiple channels are employed, the channels support and separate the needles and their respective sutures. The support may be of any suitable length n which will sufficiently support the needles.

Figure 17:
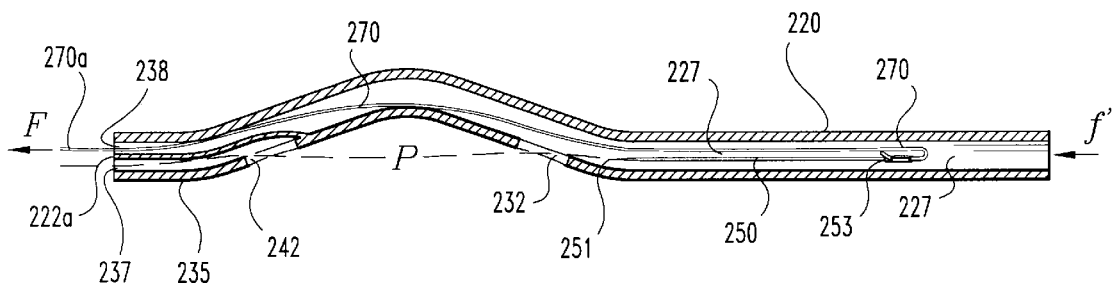
FIG. 17 is a side cross sectional view of an assembly according to one embodiment of this invention.
Figure 18:
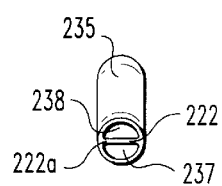
FIG. 18 is an end perspective view of the guide of FIG. 17.
Figure 19:
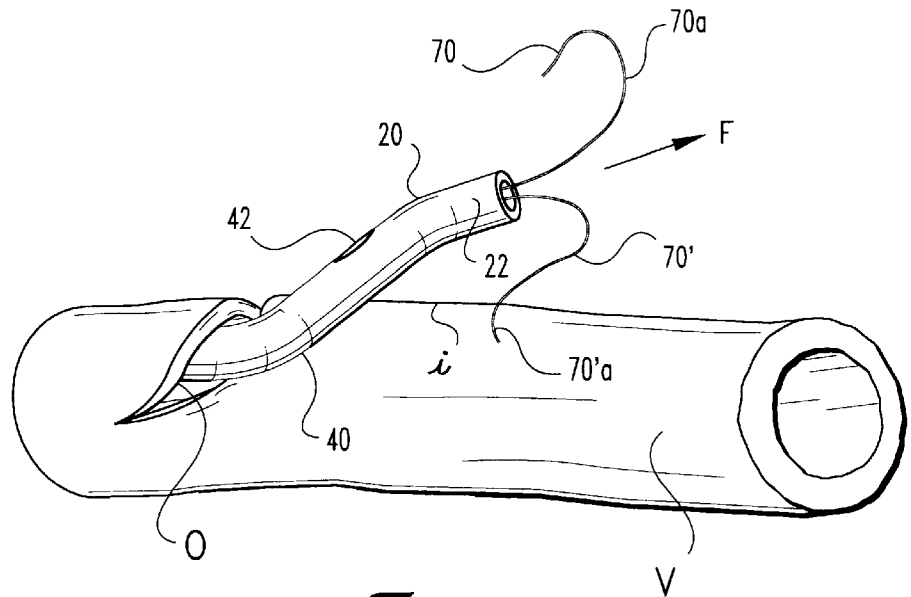
FIG. 19 is a side view of a guide assembly of this invention inserted into a wound in a vascular structure.
Figure 20:
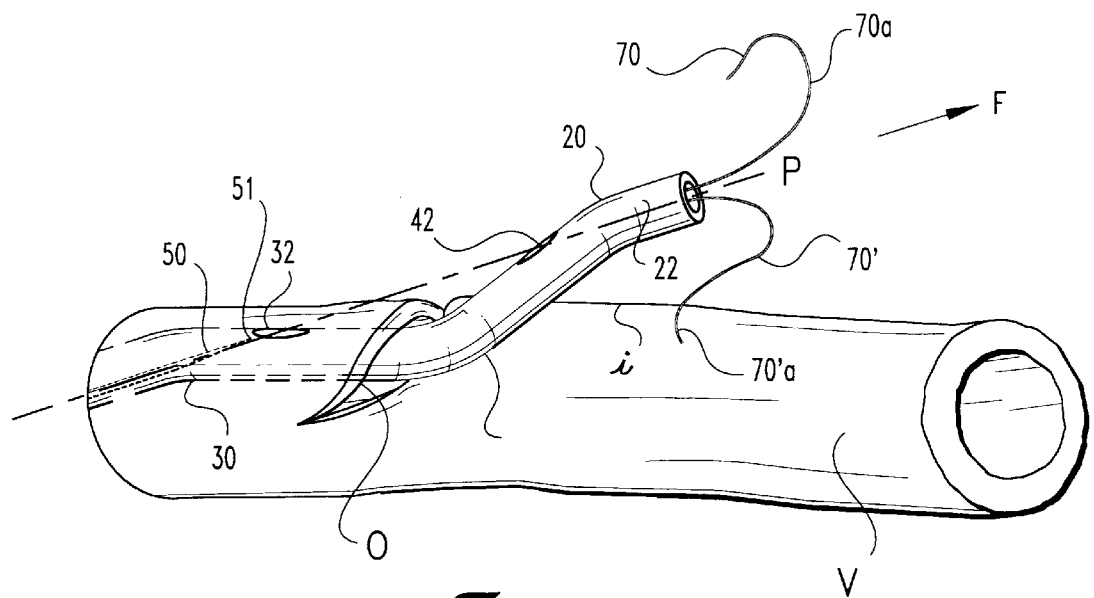
FIGS. 20–22 are side partial sectional views showing the progression of a needle along the needle path.
Figure 21:
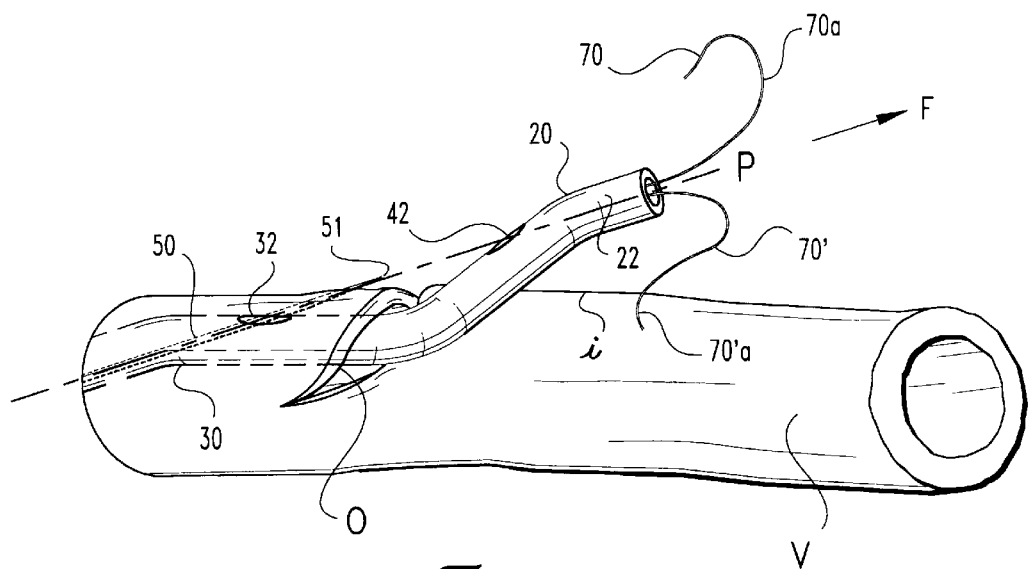
Figure 22:
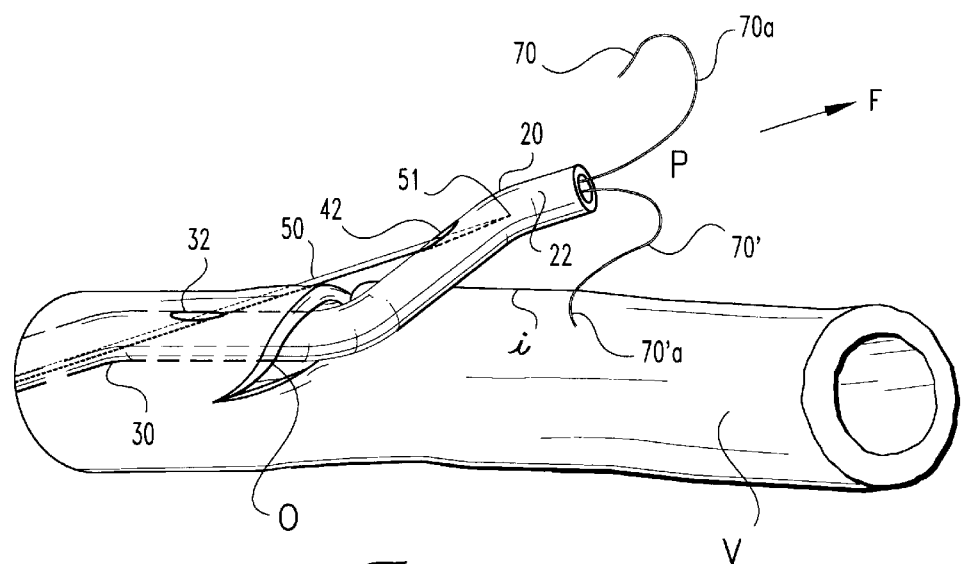

In a preferred embodiment depicted in FIGS. 17 and 18, the second portion 235 of the cannula 220 defines a suture lumen 238 parallel to the distal lumen 237. The suture lumen 238 is preferably in communication with the proximal lumen 227. In one embodiment, both the suture lumen 238 and the proximal lumen 227 are in communication with the second opening 222a. Needles 250 are loaded into the proximal lumen 227 and positioned to be deployed through the exit aperture 232, tissue and into the capture aperture 242 along the tissue path P as described above for other embodiments. Suture material 270 is loaded to extend from the opposite end 252 of the needle 250 through the proximal lumen 227, the suture lumen 238 and the second opening 222a. Applying a pulling force F to the end 270a of the suture extending from the opening 222a applies a force f' to the opposite end 253 of the needle 250 which deploys the piercing end 251 of the needle 250 through the exit 232. One advantage of providing a suture lumen 238 separate from the distal lumen 237 is that suture will not interfere with needle activites such as when it pierces the tissue edge. In most preferred embodiments, the suture lumen feature may be combined with other features of this invention such as those depicted in FIGS. 1–16. For example, the device of FIG. 17 may be provided with a ramp similar to the ramp 34 depicted in FIG. 8. The ramp would extend from the lumen wall adjacent exit 232 and form a channel for suture with the opposite surface of the lumen.

The invention also provides methods for suturing a wound in tissue. According to one embodiment a device such as depicted in FIGS. 1–18 is provided to suture a wound. The present invention is particularly useful for suturing a vascular wound after an intravascular procedure has been completed. Once the angioplasty is completed, the cannula 20 of this invention is applied to the vascular wound. The cannulas of this invention can be placed over a guide wire or through an introducer in place from the intravascular procedure. Referring now to FIGS. 19–22, the first end 21 of the cannula 20 is inserted into the wound opening O of the vascular structure V. The guide cannula 20 is manipulated so that the exit aperture 32 contacts an inner surface i of the tissue surrounding the wound. The piercing end 51 of the needle 50 is deployed through the exit aperture 32 and tissue T along the needle path P to deliver suture to the tissue T. Preferably, the needle is deployed by applying a force F on a portion 70a, 70'a of the suture 70, 70' extending from the second end 22 of the cannula 20. Preferably force F is applied along the path axis P. Because the suture 70 is reverse threaded as shown in FIG. 7 or FIG. 9, applying force F pulls the needle 50 through the lumen 27, out of the exit aperture 32 and through the tissue T. Where multiple needles are employed in the side-by-side initial position, such as depicted in FIG. 9, a particular needle can be selectively deployed by applying a force to either suture 70 or 70'.

After the needle 50 leaves the exit aperture 32, it continues its travel along the path P to the capture aperture 42. Once the piercing end 51 of the needle 50 is safely shielded within the distal lumen 37, the cannula 20 is withdrawn through the wound opening O, pulling the suture 70 through the tissue T. The needle 50 can then be returned to the initial position within the proximal lumen 27 and the cannula returned to the wound opening to deliver another suture. The cannula 20 is rotated and manipulated within the wound to position the exit aperture 32 advantageously to deliver a suture at a particular location around the wound opening O. Suture can be selectively delivered to various locations around the wound opening in this manner. The suture can be tied and knotted. The suture can then be knotted to close the wound opening using conventional methods such as by using a knot pusher which is commercially available.

The suturing assemblies of this invention can be made of any suitable, biocompatible material and in any suitable dimension for the intended application. For example, the guide cannulas may be molded plastic, stainless steel, nitinol or extruded nylon or a combination thereof, or any other suitable, biocompatible material. For vascular system structure repairs, the guides of this invention are sized for introduction into veins and arteries. Referring now to FIG. 3, in one embodiment, the guide 20 has an overall length L of 6.50 inches (165 mm). The first portion 25 has a length $l_1$ of 4.72 inches (120 mm) and the second portion 35 has a length $l_2$ of 1.5 inches (37.5 mm). The first 33a and second 33b mid-sections have lengths la, lb of about 0.39 inches (10 mm). The first 30, second 40 and third 45 bends each define an angle $\alpha_1$, $\alpha_2$ and $\alpha_3$, of about 150°. In this embodiment, the outer diameter D of the guide 20 is about 0.24 inches (6 mm) and the diameter d of the lumen 27 is about 0.16 inches (4 mm).

As should also be appreciated from the foregoing, the present invention enables the ready, effective and efficient closing of a percutaneous puncture in an artery. Thus, it is expected that this invention will be a significant advancement in the fields of cardiology and radiology. The device may allow continuance of anticoagulation therapy post-procedure, more aggressive use of thrombolytic agents and safer use of large bore catheters. It should also reduce discomfort and complication rates for patients; allow many inpatient procedures to be performed safely on an outpatient basis; reduce costs for recovery room care; decrease the time and cost of interventional procedures; and reduce exposure of hospital personnel to human blood.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A suturing assembly, comprising:
    a cannula defining
        a first end, a first portion adjacent said first end sized and configured for insertion into a wound, said first portion defining a proximal lumen for slidably receiving a needle, a first bend and a needle exit aperture at said first bend in communication with said proximal lumen, said proximal lumen and said needle exit aperture defining a needle path, and
        a second end opposite said first end, a second portion adjacent said second end and defining a distal lumen, said cannula defining a second bend between said first bend and said second portion, said second portion defining a needle entrance aperture in communication with said distal lumen and in line with said needle path; and
    a needle slidably disposed within said proximal lumen, said needle having a piercing end extendable through said needle exit aperture and said needle entrance aperture, and an opposite end slidable within said proximal lumen, said needle having a first position within said proximal lumen and a second deployed position with said piercing end in said distal lumen and said opposite end in said proximal lumen.

2. The suturing assembly of claim 1 wherein said cannula defines a first opening in said first end and in communication with said proximal lumen.

3. The suturing assembly of claim 2 wherein said cannula defines a second opening in said second end and in communication with said distal lumen.

4. The suturing assembly of claim 3 further comprising a suture secured to said opposite end of said needle and extending through said proximal lumen, said exit aperture, said entrance aperture and said second opening.

5. The suturing assembly of claim 1 wherein said cannula defines a second opening in said second end and in communication with said distal lumen and said proximal lumen communicates with said distal lumen and further comprising a suture secured to said opposite end of said needle and extending through said proximal lumen, said distal lumen and said second opening.

6. The suturing assembly of claim 5 wherein said suture is swedged to said needle.

7. The suturing assembly of claim 1 wherein said second portion defines a suture lumen parallel to said distal lumen and said cannula defines a second opening in said second end and in communication with said suture lumen.

8. The suturing assembly of claim 7 wherein said suture lumen is in communication with said proximal lumen.

9. The suturing assembly of claim 8, further comprising a suture secured to said opposite end of said needle and extending through said proximal lumen, said suture lumen and said second opening.

10. The suturing assembly of claim 1 wherein said first and second bends define a curved middle portion and said curved middle portion is composed of a rigid material.

11. The suturing assembly of claim 10 wherein said first end of said cannula is composed of a flexible material.

12. The suturing assembly of claim 1, further comprising a second needle slidably disposed within said proximal lumen, said needle having a piercing end extendable through said needle exit aperture and said needle entrance aperture and an opposite end slidable within said proximal lumen.

13. The suturing assembly of claim 12, further comprising a suture having opposite ends, each of said opposite ends of suture secured to said opposite end of one of said needles, said suture extending from said opposite ends of said needles and through said proximal lumen, said exit aperture, said entrance aperture and said second opening, said suture forming a loop outside of said second opening.

14. The suturing assembly of claim 12, wherein said first lumen communicates with said second lumen and further comprising a suture having opposite ends, each of said opposite ends of suture secured to said opposite end of one of said needles, said suture extending from said opposite ends of said needles and through said proximal lumen, said distal lumen and said second opening, said suture forming a loop outside of said second opening.

15. A suturing guide, comprising a cannula defining a first end, a first portion adjacent said first end sized and configured for insertion into a wound, said first portion defining a proximal lumen for slidingly receiving a needle, a first bend and a needle exit aperture at said first bend in communication with said proximal lumen, said proximal lumen and said needle exit aperture defining a needle path.

16. The suturing guide of claim 15, further comprising a ramp disposed within said proximal lumen at an end of said exit aperture, said ramp inclined toward said exit aperture to guide a needle along said needle path as the needle advances through said proximal lumen.

17. The suturing guide of claim 15 wherein said cannula also comprises a second portion opposite said first portion and adjacent said second end and defining a distal lumen; a second bend between said first bend and said second portion; and said second portion defining a needle entrance aperture in communication with said distal lumen and in line with said needle path.

18. A suturing assembly, comprising:
   cannula defining a single continuous lumen and including
      a first end, a first portion adjacent said first end sized and configured for insertion into a wound, said first portion defining a proximal portion of said lumen for slidably receiving a needle, a first bend and a
      needle deployment aperture at said first bend in communication with said proximal portion of said lumen, said proximal portion of said lumen and said needle deployment aperture defining a needle path, and
      a second end opposite said first end, a second portion adjacent said second end and defining a distal portion of said lumen, said cannula defining a second bend between said first bend and said second portion, said second portion defining a needle capture aperture in communication with said distal lumen and in line with said needle path; and
   a needle slidably disposed within said proximal portion of said lumen, said needle having a piercing end extendable through said needle exit aperture and said needle capture aperture, and an opposite end slidable within said proximal portion of said lumen, said needle having a first position within said proximal portion of said lumen and a second deployed position with said piercing end in said distal portion of said lumen and said opposite end in said proximal portion of said lumen.

19. The suturing assembly of claim 18, further comprising a second lumen defined in said cannula parallel to said first lumen, said second lumen in communication with said needle deployment aperture and said needle capture aperture and a second needle slidably disposed within said second lumen, said needle having a piercing end extendable through said needle exit aperture and said needle entrance aperture and an opposite end slidable within said proximal portion of said second lumen.

20. The suturing assembly of claim 18, further comprising a guide member fitted within said proximal portion of said lumen, said guide member defining a passageway therethrough for receiving a needle.

21. The suturing assembly of claim 20, further comprising a second passageway for receiving a second needle.

* * * * *